(12) United States Patent
Tsai Song et al.

(10) Patent No.: US 8,501,927 B2
(45) Date of Patent: Aug. 6, 2013

(54) VACCINE PRODUCED USING OPTIMIZED IMMOBILIZATION ANTIGEN CDNA OF CRYPTOCARYON IRRITANS AND PRODUCING METHOD AND USE THEREOF

(75) Inventors: Yen-Ling Tsai Song, Taipei (TW); Yen-Hong Lin, Taipei (TW); Jose Priya Thankaraj Alphonsal, Taipei (TW)

(73) Assignee: National Taiwan University, Taipei (TW)

( * ) Notice: Subject to any disclaimer, the term of this patent is extended or adjusted under 35 U.S.C. 154(b) by 5 days.

(21) Appl. No.: 13/239,110

(22) Filed: Sep. 21, 2011

(65) Prior Publication Data

US 2013/0071483 A1    Mar. 21, 2013

(51) Int. Cl.
*C07H 21/04* (2006.01)
*C12N 15/00* (2006.01)

(52) U.S. Cl.
USPC ........................................ 536/23.7; 435/320.1

(58) Field of Classification Search
None
See application file for complete search history.

(56) References Cited

U.S. PATENT DOCUMENTS

2010/0086613 A1    4/2010   Wu et al.

FOREIGN PATENT DOCUMENTS

TW    200926967    7/2009

OTHER PUBLICATIONS

Plotkin et al (Vaccines W. B. Saunders Company, 1988, p. 571).*

* cited by examiner

*Primary Examiner* — Albert Navarro
(74) *Attorney, Agent, or Firm* — WPAT, P.C.; Anthony King (57) ABSTRACT

The present invention provides an optimized immobilization antigen cDNA sequence of *cryptocaryon irritans*, which has been processed codon replacement and caused the cDNA to express in prokaryotic and eukaryotic cell and translate a protein has similar immunogenicity as the immobilization antigen purified from the theront of *Cryptocaryon irritans*. The present invention further provides a DNA vaccine produced using the cDNA to prevent fish form *cryptocaryon irritans* infection.

7 Claims, 3 Drawing Sheets

Figure 1

```
                                                   1 GGATTAAATAATTAAAGAA
  20 ATG  AAGATTTTAGCTATTTTATTGATTTCTTCATTAGCTGTAATCACATCAGCTGCATTTGTTAAA
     M   K  I  L  A  I  L  L  I  S  S  L  A  V  I  T  S  A  A  F  V  K  23
  89 AAAACTGCTGCTGCAGATTGGAAAGGTACATTTGTAGTTACTAAAAGTAGTTGTTTGGCAACTTGTGGT
     K  T  A  A  A  D  W  K  G  T  F  V  V  T  K  S  S  C  L  A  T  C  G 46
 158 TGGAAACTTGGTTCTACAGTTGTTATTGCTGATAAAACAGGAGTAAATACAAAAGTTACATGGGTAGGT
     W  K  L  G  S  T  V  V  I  A  D  K  T  G  V  N  T  K  V  T  W  V  G 69
 227 ACAACACATACAACTGATACTACAAATGTTGATGTTGCAGCGGGAAGTTGTAAATATATTAGTGCTGTA
     T  T  H  T  T  D  T  T  N  V  D  V  A  A  G  S  C  K  Y  I  S  A  V 92
 296 ACAACTGCTGGT  GCTGGTACACCTGCAGAAGTTGCGAATAACAATGATGAATGTGAATTTGCATCT
     T  T  A  G   A  G  T  P  A  E  V  A  N  N  N  D  E  C  E  F  A  S 115
 365 GGAACTTGCACTGTTATGGGAAGAAAA  ACAACTCCTGGAACAGTAGTTTTTAATAGAGATATGGAC
     G  T  C  T  V  M  G  R  K   T  T  P  G  T  V  V  F  N  R  D  M  D 138
 434 TTAGATACTAAGCCTTTACAAATCCTATATAAG  TTTGAAATGATAGCAAAATCATCAACCAGTGTA
     L  D  T  K  P  L  Q  I  L  Y  K   F  E  M  I  A  K  S  S  T  S  V 161
 503 AAAGCTGCTGCCGAT  GGTGCAGACTGTGATACT  GCTTCATTAGTAGATATAACTACTGATGCT
     K  A  A  A  D   G  A  D  C  D  T   A  S  L  V  D  I  T  T  D  A 184
 572 AAACCTATTGTAGGAACATTAAAACTTTCTAAAGCTACTTGTGATAAATGTTCATGGGATATAACTAAA
     K  P  I  V  G  T  L  K  L  S  K  A  T  C  D  K  C  S  W  D  I  T  K 207
 641 GATTTAAAAATTACA  GATGCTACAAATAAATATATGGTCACACTTGCAGGAACTATCAAAGAAACT
     D  L  K  I  T   D  A  T  N  K  Y  M  V  T  L  A  G  T  I  K  E  T 230
 710 GCTACTGGTGATTGTAAAAATAAACTTACAGCATCTGAAACATGCTATGTCACAAAAAAAGATGACAAA
     A  T  G  D  C  K  N  K  L  T  A  S  E  T  C  Y  V  T  K  K  D  D  K 253
 779 ACTTTCATTCTTGTTAGCTGTACTACTCTTGATACAACCGGTTCAGGTATTCCAATCGTCATATCAACT
     T  F  I  L  V  S  C  T  T  L  D  T  T  G  S  G  I  P  I  V  I  S  T 276
 848 GTAAATTCAAAAACTACTTTAACCTTGACATGGAAAGATGCAACTGCT  GCATGTAATGTTGTTGGA
     V  N  S  K  T  T  L  T  L  T  W  K  D  A  T  A   A  C  N  V  V  G 299
 917 GAAGTTAGTTCAACTAGTGGAGCAAATTCTCTGAAATTATTTACAGGATTAAGTGTTATGCTAATCCTC
     E  V  S  S  T  S  G  A  N  S  L  K  L  F  T  G  L  S  V  M  L  I  L 322
 986 ACCTTTGCTCTTTTATTCAAATGAGGAATATTGGATCATATTTTGATAAAAATATCTATATAAAGCATA
     T  F  A  L  L  F  K 329
1055 ATTAGTTTAATTTTTTGATATTCTTGAATTTAGTACTTAAATAATTTTATATTTTATGCTAAAAGATCT
1124 AAATTACAAAAAAAAAAAAAAAAAA 1149
```

VACCINE PRODUCED USING OPTIMIZED IMMOBILIZATION ANTIGEN CDNA OF CRYPTOCARYON IRRITANS AND PRODUCING METHOD AND USE THEREOF

FIELD OF THE INVENTION

The present invention relates to a *Cryptocaryon irritans* vaccine produced by an immobilization antigen cDNA of *Cryptocaryon irritans*, which is able to translate into protein containing the same immunogenicity as the original protein of *Cryptocaryon irritans*.

DESCRIPTION OF PRIOR ART

The holotrichous ciliated protozoan parasite *Cryptocaryon irritans* is the causative organism of white spot disease in a broad range of marine fishes. Wild, ornamental and cultured fish species are included in the list. This parasite has become a frequent pest in fish farms and is considered as one of the most devastating parasites widely distributed. Not only Asian (China, Taiwan, Korea, Japan, India, and other Asian countries) fishing industry, but also Australia, Persian Gulf, Israel, Red Sea, and Caribbean Sea have been impacted by *C. irritans* infection. Mass mortalities of fishes caused by this parasite often result in large economic losses in mariculture. The use of chemotherapeutic agents available to treat fish for *C. irritans* infection are creating environmental pollution problem and deemed unsafe for human consumption.

The life cycle of *C. irritans* consists of four development stages: parasitic trophonts, protomonts leaving the hosts, tomonts cysts in seawater, and free swimming theronts released from tomonts. Earlier works on *Ichthyophthirius multifiliis*, a freshwater ciliate parasite belonging to a taxonomically different phylum, revealed that humoral immunity confers resistance by immobilizing the theronts. Fish serum and skin mucosal immunity play important roles against *C. irritans* infection. Infiltration of leukocytes in the infected site and the localization of $CD8^+$ lymphocytes on trophonts from naturally infected fish reveal the activation of cellular immune responses against *C. irritans*. Non-specific cellular immune responses such as down-modulation of eosinophil population in the peripheral blood and proliferation of mucus cells in the epidermal layer were also conferred in immunized grouper against *C. irritans*.

Some prior arts have shown that immunization with theronts, trophonts and tomonts of *C. irritans* can elicit stronger protective immunity in infected fish and confirmed that the theront stage of *C. irritans* can provide stronger protective immunity in fish. As an obligate parasite, *C. irritans* theronts used as vaccine can only be obtained from infected fish. Hence, collection of sufficient quantities of theronts by infecting large number of live fish for vaccine production is very time-consuming, costly and impractical. Until now, the absence of culture technique to grow the protozoan in vitro is a major obstacle in the technology aimed at developing prevention and control measures for *C. irritans*.

An immobilization phenomenon occurs when sera and mucus from immune fish immobilize live parasites in vitro and this effect corresponds to protection in vivo. It was found that antibody binding to parasite cell and ciliary surface antigens cause immobilization. The target antigens of immobilization are immobolization antigens (iAg), characterized as a class of highly abundant, glycosyl phosphatidyl inositol (GPI) anchored surface membrane proteins. An iAg was isolated from parasite *I. multifilis* and was found to play key roles in the elicitation of protective immunity. Vaccination with recombinant iAg gene fragments has been shown as effective against *Ichthyophthirius multifillis* in goldfish. Some researchers extracted integral membrane proteins of *C. irritans* and an abundant surface antigen of theronts and trophonts were detected by antiserum from infected fish or immunized rabbits. This surface agglutination/immobilization antigen was purified and cloned from the serotype G37 of *C. irritans*. The iAg DNA sequence is difficult to be expressed in *E. coli* and eukaryotic cells, because bacteria and eukaryotic cells fail to use the parasite codon language. The codon optimized iAg (LISA-32) subcloned into pHSG299 construct can be expressed only in bacteria but cannot express in mammalian cells, insect cells or yeast cells. In the present invention, we modified the codons of iAg and successfully expressed the iAg recombinant protein in *E. coli* as well as in fish cells. The present invention further proved that the codon changed iAg is immunogenic. The immunization tests revealed that this codon-changed iAg can be a promising DNA vaccine against *C. irritans* infection in the grouper *E. coioides* and in other marine fishes as well.

DNA vaccination is a technique for protecting an organism against disease by injecting it with genetically engineered DNA to produce an immunological response. Nucleic acid vaccines are still experimental, and have been applied to a number of viral, bacterial and parasitic models of disease, as well as to several tumour models. DNA vaccines have a number of advantages over conventional vaccines, including the ability to induce a wider range of immune response types.

As for human, vaccines are among the greatest achievements of modern medicine—in industrial nations, they have eliminated naturally occurring cases of smallpox, and nearly eliminated polio, while other diseases, such as typhus, rotavirus, hepatitis A and B and others are well controlled. Conventional vaccines, however, only cover a small number of diseases, and infections that lack effective vaccines kill millions of people every year, with AIDS, hepatitis C and malaria being particularly common.

First generation vaccines are whole-organism vaccines—either live and weakened, or killed forms. Live, attenuated vaccines, such as smallpox and polio vaccines, are able to induce killer T-cell (TC or CTL) responses, helper T-cell (TH) responses and antibody immunity. While killed vaccines do not have this risk, they cannot generate specific killer T cell responses, and may not work at all for some diseases. In order to minimize these risks, so-called second generation vaccines were developed. These are subunit vaccines, consisting of defined protein antigens (such as tetanus or diphtheria toxoid) or recombinant protein components (such as the hepatitis B surface antigen). These, two, are able to generate TH and antibody responses, but not killer T cell responses.

DNA vaccines are third generation vaccines, and are made up of a small, circular piece of bacterial DNA (called a plasmid) that has been genetically engineered to produce one or two specific proteins (antigens) from a pathogen. The vaccine DNA is injected into the cells of the body, where the "inner machinery" of the host cells "reads" the DNA and converts it into pathogenic proteins. Because these proteins are recognized as foreign, when they are processed by the host cells and displayed on their surface, the immune system is alerted, which then triggers a range of immune responses. These DNA vaccines developed from "failed" gene therapy experiments. The first demonstration of a plasmid-induced immune response was when mice inoculated with a plasmid expressing human growth hormone elicited antibodies instead of altering growth.

As for animals, vaccination and inoculation play an important role in preventing animal diseases and in the development of aquiculture. Fish vaccines include inactivated vaccine, live attenuated vaccine, recombinant inactivated vaccine, genetic engineering vaccine, and DNA vaccine, and there are some commercial vaccines against bacteria in the past decade, however, there are few vaccines against viruses, and few vaccines against parasites. Furthermore, most of the fish vaccines are used in lab and not suitable for commercial market. This is because of the concerning about immunogenicity, production cost, and safety.

DNA vaccine has been paid close attention since 1993 for its high immunogenicity, which brings the recombinant gene of antigen into animal cells directly by transfection or injection, and expresses natural antigens. Compare to the traditional vaccine, DNA vaccine has the advantages of low cost, simple production process, easy to transportation, and without the risk of reversion to virulence. The mechanism of DNA vaccine is similar to the inactivated vaccine, but DNA vaccine does not have the risk of infection, and has better efficiency than the live attenuated vaccine and the subunit vaccine.

The first report of DNA vaccination for a viral disease in fish (rainbow trout, Oncorhynchus mykiss) was made by Anderson et al. in 1996, a DNA vaccine for infectious pancreatic necrosis virus (IPNV) by a plasmid comprising the glycoprotein gene G of the virus, and there are many researches and inventions about the DNA vaccines used for fish till now.

The present invention provides a vaccine produced using optimized immobilization antigen cDNA of *Cryptocaryon irritans* and producing method and use thereof, wherein the vaccine is a fish vaccine against parasite, which is an invention with novelty and obviousness in the arts.

SUMMARY OF THE INVENTION

The present invention provides a nucleic acid-based vaccine comprising the optimized immobilization antigen cDNA of *Cryptocaryon irritans*, an optimized immobilization antigen cDNA of *Cryptocaryon irritans*, a vector comprising the optimized immobilization antigen cDNA of *Cryptocaryon irritans*, and a method for optimizing an immobilization antigen cDNA sequence of *Cryptocaryon irritans*.

The present invention further provides an optimized immobilization antigen cDNA of *Cryptocaryon irritans* in production of an antibody against *Cryptocaryon irritans* by a host.

DETAILED DESCRIPTION OF THE INVENTION

The term "suitable codon" is defined as a codon which can be replaced to a codon of a nucleotide chain without significant conformation change of the protein deduced by the codon replaced nucleotide chain. In other word, "the suitable codon" is suitable for the codon replaced nucleotide chain.

The term "similar immunogenicity" is defined as two antigens, such as proteins, have the same ability to elicit immune responses to the same antigen of a pathogen, although the two antigens may have different structures, molecular weights, sources or production methods.

The present invention provides a method for optimizing an immobilization antigen cDNA of *Cryptocaryon irritans* comprising the following steps:
  a. extracting mRNA of an immobilization antigen of *Cryptocaryon irritans*;
  b. converting the mRNA into cDNA sequence;
  c. determining a suitable codon corresponding to a specific amino acid based on at least one specific characteristic deduced from the neighbor residues of a stop codon of the cDNA sequence, to get a protein translated from the cDNA sequence which is replaced at least one of the stop codon to the suitable codon, and has similar immunogenicity as the immobilization antigen purified from the theront of *Cryptocaryon irritans*; and
  d. replacing the stop codon of the cDNA to the suitable codon to produce optimized cDNA sequence;
wherein the specific characteristic is selected form the group consisting of structural property, hydrophobicity and charge distribution deduced from the neighbor residues of the stop codon.

In the method of the present invention, the specific amino acid is glycine, alanine, or arginine, wherein glycine was placed at regions with hydrophobicity alteration, alanine substitution was to minimize structural change, and arginine was adopted for regional charge considerations.

The present invention further provides an optimized immobilization antigen cDNA of *Cryptocaryon irritans* comprising the nucleotide sequence of SEQ ID NO: 10, and a vector comprising the optimized immobilization antigen cDNA of *Cryptocaryon irritans* comprising the nucleotide sequence of SEQ ID NO: 10. pGEX-2T from GE Healthcare, formerly Amersham Biosciences. Catalogue number: 27-4801-01, or pcDNA3.1(+) from Invitrogen Life technologies, Catalog no. V790-20 serves as the expression vector.

The present invention further provides a nucleic acid-based vaccine comprising the optimized immobilization antigen cDNA of *Cryptocaryon irritans* comprising the nucleotide sequence of SEQ ID NO: 10, and the nucleic acid-based vaccine is able to be encapsulated by water/oil/water triple layer emulsions or chitosan nanoparticles.

The present invention further provides a use of the optimized immobilization antigen cDNA of *Cryptocaryon irritans* in production of an antibody against *Cryptocaryon irritans* by a host, characterized in stimulating the host to produce antibodies against the protein translated from the optimized immobilization antigen cDNA of *Cryptocaryon irritans* by treating the host with a vector comprising the nucleotide sequence of SEQ ID NO: 10, wherein the vector is pGex2T-iAg or pcDNA3.1-iAg, encapsulated by water/oil/water triple layer emulsions or chitosan nanoparticles and mixed into feeding stuff or bait, or added into water for soaking the host, or injected into the host, and the host is an aquatic organism, specifically targeted to fish, such as grouper, *Acanthopagrus schlegelii, Caprodon schlegelii, Cephalopholis aurantia, Cephalopholis miniata, Dentex dentex, Dicentrarchus labrax, Diplodus puntazzo, Diplodus sargus, Epinephelus awoara, Epinephelus coioides, Epinephelus lanceolatus, Epinephelus trimaculatus, Girella leonina, Hapalogenys mucronatus, Kentrocapros aculeatus, Larimichthys crocea, Lates calcarifer, Lutianus argentimaculatus, Lutj anus erythopterus, Lutj anus stellatus, Melichthys vidua, Pagrus major, Plectorhynchus cinctus, Poecilia latipinna, Pterois volitans, Rhabdosargus sarba, Scatophagus argus, Seriola dumerili, Siganus oramin, Sparus aurata, Trachinotus blochii, Rachycentron canadum, Seriola quinqueradiata, Amphiprion clarkii, Amphiprion frenatus, Amphiprion polymnus*, or *Amphiprion ocellaris*.

BRIEF DESCRIPTION OF THE DRAWINGS

FIG. 4.

Bright (A), DAPI stained (B), FITC stained (C) and merged (D) fields of grouper GF-1 cells stained with rabbit Ig against *C. irritans* theronts via confocal microscopy. (a-d: GF-1 cells transfected with iAg plasmid (pcDNA3.1-optiAg); e-h: GF-1 cells transfected with mock plasmid (pcDNA3.1); and i-1: GF-1 cells without transfection. Bar=50 nm.

FIG. 5.

Kaplan-Meier survival curve showing the mortality of iAg immunized fish. The log rank significance is 0.008 for both the iAg immunized and rec iAg boosted group.

EXAMPLE

Parasite Collection, Maintenance and Propagation

*Cryptocaryon irritans* infected fish were sourced out from a live fish market in Taipei, Taiwan. Tomonts were collected from the bottom of the tank after the exit from host fish and were maintained in grouper *E. coioides* fingerlings each with 2.6 g average body weight (BW) and purchased from a hatchery in southern Taiwan. The maintenance procedure was as follows: tomonts were gently collected from the bottom of the tank by means of a small paint brush, cleaned of any debris and mucus by repeated washing in sea water, transferred to petri plates with filtered seawater and cultured for 3-7 days in room temperature. Theronts that emerged from the tomont cysts were collected by centrifugation at 1500 g at 4° C. for 10 minutes. Pellets containing viable theronts were re-infected and propagated in naive adult fish (ca. 300 g BW each, procured from a live fish market). Then, around $6 \times 10^6$ viable theronts were collected for challenge experiment by waterborne infection.

Parasite
DNA Extraction and Genotype Differentiation of *C. irritans*

20~30 tomonts were taken for DNA extraction using Bio-Rad 36897 CHELEX 100 resin. The DNA was then amplified using the polymerase chain reaction (PCR) with specific primers for 18S and ITS-1 region of the rDNA (Primers 1 (SEQ ID NO: 1) and 2 (SEQ ID NO: 2); Table 1). Thermal cycling was carried out with the following program: an initial denaturation at 95° C. for 3 min, then 30 cycles of denaturation at 95° C. for 60 s, annealing at 55° C. for 30 s, extension at 72° C. for 60 s, followed by a final elongation at 72° C. for 5 min Amplified products were sequenced by Mission & Co., Taipei. Nucleotide sequences of partial 18S, entire ITS-1 and part of 5.8S regions of *C. irritans* were analyzed to identify the genotype using CLUSTAL W (version 1.83), a multiple sequence alignment program.

The DNA sequences of partial 18S, entire ITS-1 and partial 5.8S rDNA of two isolates of *C. irritans* tomonts were obtained. The nucleotide sequences are available in the GenBank, i.e. Chiayi (AF490381) and Aus C (AY029271).
cDNA Cloning of Immobilization Antigen
Partial Amplification of iAg Total RNA was extracted from theronts using Trizol (Invitrogen) as described in manufacturer's protocol. Primers specific to iAg were designed by Primer 3 (SEQ ID NO: 3) based on the recorded iAg sequence (AB262047) in GeneBank database. The partial nucleotide sequence of iAg gene from *C irritans* Chiayi isolate was amplified by SuperScript™ III One-Step RT-PCR System in a 50 µl reaction volume containing 25 µl 2× Reaction Mix, 10 pM primer set (primers 3 (SEQ ID NO: 3) and 4 (SEQ ID NO: 4), Table 1), 2 µl SuperScript™ III RT/Platinum®Taq Mix and 0.5 µg RNA template. RT-PCR amplification was as follows: cDNA synthesis at 50° C. for 30 min and direct denaturation at 94° C. for 2 min, then 40 cycles of 94° C. for 15 s, 55° C. for 30 s, and 68° C. for 1 min, followed by a final elongation at 68° C. for 5 min Amplified products were subcloned into the pGEM-T Easy Vector (Promega) and sequenced.
3' and 5' Rapid Amplification of cDNA Ends The complete cDNA sequence of iAg gene from Chiayi isolate was obtained by 5' and 3' rapid amplification of cDNA ends (RACE) kits (Invitrogen & Clontech). For 3'RACE, the first-strand cDNA was synthesized by reverse transcription in a 20 µl reaction containing 2 µl of 10×PCR buffer (Invitrogen), 2.5 mM $MgCl_2$, 0.5 mM dNTP, 5 mM DTT, 200 U Superscript II Reverse transcriptase and oligo (dT)-containing Adaptor Primer (AP; Invitrogen) at 42° C. for 50 mM following a termination at 70° C. for 10 mM Then the 3' end of the cDNA was amplified by PCR in a 50 µl reaction containing 5 µl 10×PCR buffer, 5 mM $MgCl_2$, 0.5 mM dNTP, 5 mM DTT, 5 U of Taq (Genemark), 10 µM gene specific primer (primer 5 (SEQ ID NO: 5), Table 1), 10 µM Abridged Universal Amplification Primer (AUAP; Invitrogen) which is complementary to AP and 2 µl of cDNA template. PCR amplification was as follows: initial denaturation at 94° C. for 2 mM, then 35 cycles of 94° C. for 30 s, 58° C. for 30 s, and 72° C. for 1 mM, followed by a final elongation at 72° C. for 10 min. Amplified products were subcloned into the pGEM-T Easy Vector and sequenced.

For 5'-RACE, the first-strand cDNA was synthesized using SMART™ RACE cDNA Amplification Kit (Clotnech) with 5'-RACE CDS Primer A and SMART II A Oligonucleotide at 42° C. for 1.5 h. After diluting 10×, 2 ml cDNA was added into a PCR reaction containing universal Primer A Mix (UPM; Clontech) and a reverse gene specific primer (primer 6 (SEQ ID NO: 6), Table 1). The amplification was performed at 94° C. for 2 mM, then 35 cycles of 94° C. for 30 s, 55° C. for 30 s, and 72° C. for 1 min, followed by a final elongation at 72° C. for 10 mM A nested PCR reaction included 50-100× diluted first PCR product as template, nested universal Primer A (NUP; Clontech), nested reverse gene specific primer (primer 7 (SEQ ID NO: 7), Table 1) was carried out in the same condition described above. Amplified products were subcloned into the pGemTeasy plasmid (Promega) and sequenced. The full length sequence of Chiayi iAg was examined for signal peptide by SignalP 3.0, transmembrane segments predicted by SMART program and the potential omega (ω) site for propeptide cleavage and glycosylphosphatidylinositol (GPI) anchor site predicted by the big-PI Predictor program.

Codon Replacement

The original sequence of iAg (GenBank: FJ167511) was analyzed by DNASTAR Lasergene 6 software, and the stop codons were replaced with suitable amino acids based on the structural properties, hydrophobicity and charge distributions deduced from neighbor residues. Specifically, glycine was placed at regions with hydrophobicity alteration, alanine substitution was to minimize structural change, and arginine was adopted for regional charge considerations. The designated residue replacement included Nts: 309-311 and Nts: 393-395, 468-470, 519-521, 540-542, 657-659, and 897-899. The stop codon replaced iAg sequence was further analyzed by GENEART Gene optimizer Sequence Analysis (Prisma Biotech Co.). The criteria included GC content and codon quality assessment to allow high and stable expression rates in *E. coli* as well as mammalian, insect or yeast. The average GC content was adjusted to 47% from the original 36%.

The optimized immobilization antigen cDNA of *Cryptocaryon irritans* was shown in Tablet and SEQ ID NO: 10.

Preparation of iAg Plasmid Constructs and Encapsulation

Two iAg plasmids were constructed; pGex-2t-iAg for expression in *E. coli* and pcDNA3.1-optiAg for both expression in GF-1 and ultimately for vaccination in grouper.

Cloning detail of pcDNA 3.1-optiAg: For the generation of pcDNA3.1-optiAg, iAg DNA corresponding to the mature protein without the signal peptide was obtained by PCR using a pair of primers from the codon replaced iAg template (pMAT-iAg). The amplified DNA was eluted from agarose using gel extraction kit (BIOMAN) and restricted with BamHI and EcoRI (Invitrogen) and further cloned into the BamHI and EcoRI sites of pcDNA3.1.

Cloning detail of pGEX2T-optiAg: Firstly, the iAg DNA corresponding to the mature protein without the signal peptide was obtained by PCR using a pair of primers from the codon replaced iAg template (pMAT-iAg). The amplified DNA was eluted from agarose using gel extraction kit (BIOMAN) and restricted with BamHI and EcoRI (Invitrogen) and further cloned into the BamHI and EcoRI sites of pGex-2t.

pGEX-2T is from GE Healthcare, formerly Amersham Biosciences. Catalogue number: 27-4801-01, and pcDNA3.1 (+) is from Invitrogen Life technologies, Catalog no. V790-20.

For the generation of pGex-2t-iAg, iAg DNA corresponding to the mature protein without the signal peptide was obtained by PCR using a pair of primers (primers 8 (SEQ ID NO: 8) and 9 (SEQ ID NO: 9), Table 1) from the codon replaced iAg template (pMAT-iAg). PCR amplification was as follows: initial denaturation at 94° C. for 2 min, then 35 cycles of 94° C. for 30 s, 58° C. for 30 s, and 72° C. for 1 min, followed by a final elongation at 72° C. for 10 min The amplified DNA was eluted from agarose using gel extraction kit (BIOMAN) and restricted with BamHI and EcoRI (Invitrogen) and further cloned into the BamHI and EcoRI sites of pGex-2t. Similarly, to generate pcDNA3.1-optiAg, the iAg fragment was restricted from pGex-2t-iAg using BamHI and EcoRI restriction enzymes and further ligated into the BamHI and EcoRI sites of pcDNA3.1.

For immunization purpose, the iAg plasmid construct pcDNA3.1-optiAg was encapsulated in water/oil/water triple layer emulsions of 19±6.47 nm diameter (Hsin-Yiu Chou, ROC patent application no. 200926967). Mock plasmid pcDNA3.1 as negative control and water as blank control were also encapsulated and used.

Bacterial Expression of iAg and Collection of Recombinant Protein

The iAg plasmid pGex2T-iAg was transformed into *E. coli* (pLysS BL21) and the overnight culture of *E. coli* pLyss BL21 harboring pGex-2T-iAg was diluted to 1:20 in fresh LB medium containing 50 µg/ml ampicillin and grown at 37° C. with vigorous shaking. Isopropyl 1-thio-P-o-galactoside (IPTG) was added to a final concentration of 0.1 mM when the $OD_{600}$ reached about 0.7. Bacterial cells were harvested 3 h after the addition of IPTG by centrifugation at 2000 g at 4° C. for 15 min The bacteria cells were resuspended in 300 µl of phosphate-buffered saline (PBS), boiled in SDS-sample buffer for 5 min, and analyzed by SDS-polyacrylamide gel electrophoresis. The GST-iAg fusion protein was purified by Glutathione resin (Bioman Scientific Co. Ltd, Taiwan). Briefly, 100 mL of bacterial culture after IPTG induction was harvested by centrifugation and resuspended in 10 ml of lysis buffer (50 mM Tris, pH 8.0, 0.1M NaCl, 1 mM EDTA), to which lysozyme was added to a final concentration of 5 mg/ml. After incubation at room temperature for 5 min, bacterial cells were lysed with 1% Triton-100. $MgCl_2$ and DNase I were then added to make final concentrations of 5 mM and 10 kg/ml, respectively, to digest viscous DNA. The lysate was then cleared by centrifugation. The supernatant was incubated in 1 ml of 50% slurry of Glutathione resin at room temperature for 1 h with gentle agitation. The resin was then washed three times in 10 bed volumes of PBS. The GST-iAg fusion protein was eluted from the resin with 15 mM reduced glutathione (Bioman, Taiwan). The concentration of GST fused iAg protein was measured using Bradford Assay and western blot was done. Q4 The primary antibody used was rabbit immunoglobulin raised against *C. irritans* theront (1:1000 dilution) and the secondary antibody used was alkaline phosphatase conjugated goat anti-rabbit Ig (1:1000 dilution).

Expression Analysis of iAg in GF-1 Cells

Transfection

GF-1 cells, derived from the fin tissue of grouper, *Epinephelus coioides*, was grown at 28° C. in antibiotic-added L15 medium (Invitrogen, Carlsbad, Calif.) supplemented with 5% (v/v) heat-inactivated fetal bovine serum (FBS). The majority of GF-1 cells are fibroblast-like and some are epithelioid cells. The pcDNA3.1-optiAg and the mock control pcDNA3.1 were transfected into GF-1 cells using lipofectamine 2000 (Life Technologies, Inc., Rockville, Md.) based on Manufacturer's instructions. Briefly, 20 h before transfection, $1 \times 10^5$ cells were seeded onto each well of a 6 well plate. At the time of transfection, 3 µl of lipofectamine was diluted in 100 µL15 medium. Similarly, 1 µg of iAg plasmid (pcDNA3.1-iAg) was diluted in 100 µL L15 medium. Then, the plasmid solution was then mixed into the lipofectamine solution (1:1) and kept for 20 min at room temperature. After the incubation, 800 µL of serum-free medium mixed with the plasmid-lipofectamine complex was then added drop wise onto the cells. Without disturbance, the culture plates were kept at 28° C. for 5 h and then replaced with fresh medium. At 24 h, 48 h and 72 h post transfection, the cells were harvested for detection of iAg transcript.

RT-PCR

RNA was extracted from the transfected GF-1 cells by Trizol (Invitrogen). RT-PCR was performed using the Superscript One-Step RT-PCR Kit (Invitrogen) using primers 8 (SEQ ID NO: 8) and 9 (SEQ ID NO: 9) (Table 1). The reaction condition for PCR was 1 cycle (94° C., 2 min), 30 cycle (94° C., 30 s; 55° C., 30 s; 72° C., 30 s), and 1 cycle (72° C., 10 min) The products were analyzed by electrophoresis on a 1.5% agarose gel stained with ethidium bromide.

Immunocytochemistry (ICC)

GF-1 cells were grown on thick coverslips and transfection was done as detailed above. For each transfection, 5 μg of iAg plasmid (pcDNA3.1-optiAg) was used for transfection. After 48 h transfection, cells were washed with L-15 medium and fixed in 4% paraformaldehyde (v/v) in PBS. The fixed cells were incubated with NET-gelatin blocking solution for 1 hr at room temperature. Then, the cells were permeated by immersing in PBST (PBS with 0.1% triton X-100) for 15 min at room temperature. The permeated cells were kept in 1:1000 dilution of rabbit Ig against theront in NET-gelatin solution for overnight at 4° C. Rabbit preimmune Ig was used as the first antibody control. After rinsing in PBST, cells were further incubated in 1:2000 dilution of fluorescein isothiocyanate (FITC) conjugated goat anti-rabbit Ig for 2 h at room temperature. The cells were then rinsed in PBST and stained with DAPI (4',6-diamidino-2-phenylindole) for 10 min at room temperature. After the stain solution was removed, the coverslips were picked up and placed on a microscopic slide on which a drop of mounting medium (malinol NX) was added. The coverslips were mounted in such way that the cell side face down to the slide. After drying, the slides were visualized using the confocal laser scanning microscope (Technology commons, National Taiwan University).

Immunization in Grouper Fingerlings

Primary Immunization

Grouper fingerlings without showing the clinical signs of cryptocaryonasis were brought from aquatic animal center of National Taiwan Ocean University and were acclimated 2 weeks prior to the experiment. Fish were maintained in 32 ppt sea water at 27° C. with continuous aeration. Before the immunization trials, 20% of the experimental fish were randomly selected and screened using specific serum antibody titer against *C. irritans* theronts using ELISA. A total of 21 grouper fingerlings with body weight (BW) ranging from 13-28 g were divided into three groups and held in separate tanks (38×25×26 cm). The three groups of fish were immunized as follows: (1) fish in the first group was intramuscularly injected (i.m) at the base of the dorsal fin with encapsulated water as blank control, (2) fish in the second group was injected with encapsulated mock plasmid pcDNA3.1 at a dose of 1 μg/g fish and (3) fish in the third group were injected with encapsulated iAg plasmid pcDNA3.1-optiAg at a dose of 1 μg/g fish. There were about $1.4 \times 10^{11}$ plasmid copies in 1 μg wet weight. Q6 A second time injection was given with similar dose of iAg plasmid to the test fish after 2 days of primary immunization in order to make sure the fish get enough amount of DNA injected.

Transcript Check in Fish after Primary Immunization

In vivo gene expression was examined in fish (n=3) after primary immunization. At the site of injection (muscle), iAg gene transcription was checked with iAg-specific primers 8 (SEQ ID NO: 8) and 9 (SEQ ID NO: 9) (Table 1).

Boost Immunization with Recombinant iAg Protein

A DNA prime-protein boost regimen was used in the second trial. Grouper fingerlings with body weight (BW) ranging from 30-45 g were used in this trial. This trial consisted of three groups with three replicates, each containing 12-15 fish Immunization was carried out as follows: (1) first group received immunization via intramuscular (i.m.) injection at the left side of dorsal fin base with encapsulated water as blank control; (2) second group received i.m. injection with encapsulated mock plasmid pcDNA3.1 at a dose of 1 μg/g fish; (3) third group received i.m. injection with 1 μg/g fish encapsulated iAg plasmid, followed by GST fused iAg recombinant protein given as booster immunization at a dose of 1 μg/g fish at the right side of dorsal fin base at 10 days post primary immunization.

Challenge by Water-Borne Infection

Fish were challenged by water-borne infection of live theronts at 7 days post immunization or boost. In both trials, theronts of Aus C isolate (sourced out from infected fish *Caprodon schlegelii*, from Keelung, Taiwan) were used for challenge in $1.8 \times 10^4$/liter of sea water. The challenging duration was 10-20 min in 5 liter sea water in a tank of 38×25×26 cm, and then sea water was added to make a volume of 15 L for 24 h. The appearance of white spots on the body surface from 2 to 3 days after infection was considered a specific infection. Number of dead fish was recorded daily until one week post challenge.

Documentation of Fish Mortality

The cumulative mortality of the specific death (CMSD) was calculated based on the following formula:

CMSD(%)=(Total number of dead fish−nonspecific death/Total number of test fish−nonspecific death)×100

And the relative percent survival (RPS) was calculated as follows:

RPS(%)=[1−(CMSD in the immunized group/CMSD in the control group)]×100

Statistics

The differences in the mean of CMSD (%) were analyzed using ANOVA and Duncan's new multiple range test. $p<0.01$ and $p<0.05$ were considered statistically significant. Kaplan-Meier survival curve was drawn using statistical package software SPSS 11.5 to express the mortality of iAg immunized fish.

Results of the Above Embodiment cDNA cloning of Immobilization Antigen

Figure 1:
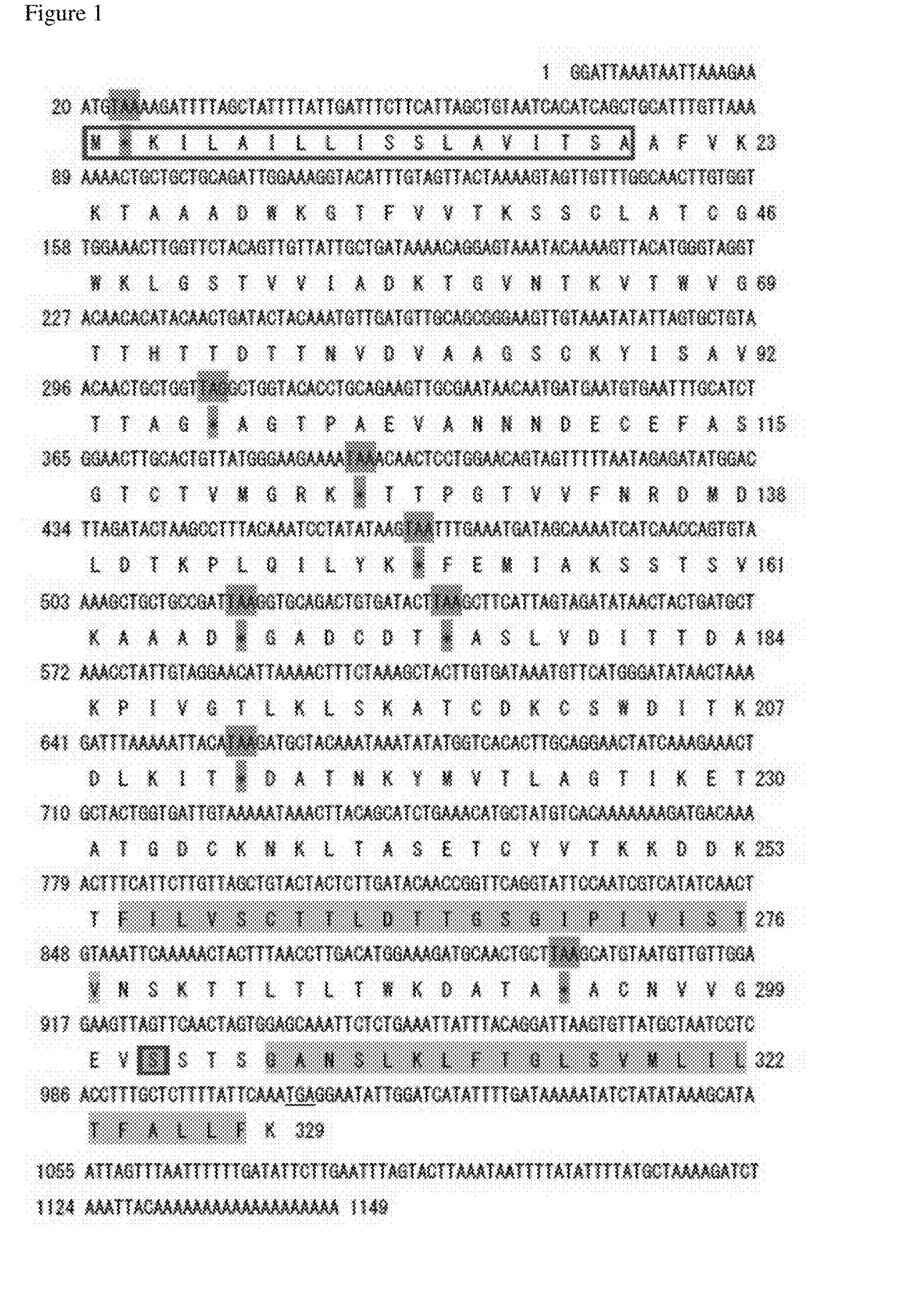
FIG. 1. Chiayi iAg nucleotide (GenBank FJ167511) & deduced amino acid sequences. Predicated signal peptide is in red box. Stop codons are shaded with green color. Grey shaded regions are the predicted transmembrane segments. Red shadow box is the position of the potential omega (ω) site in propeptide cleavage and glycosylphosphatidylinositol (GPI) anchor site (Ser 302). The numbers representing the nucleotide sequence are labeled on the left side and those for amino acid sequences are labeled on the right side.

The full length Chiayi-iAg cDNA contained a 987-bp open reading frame encoding 329 amino acids, including a putative 19-amino acid residue N-terminal signal peptide (FIG. 1). The 5' and 3' UTR were of 19 nt and 140 nt, respectively. In the gene sequence of Chiayi-iAg, seven TAA codons (Nts: 23-25, 392-394, 467-469, 518-520, 539-541, 656-658 and 896-898) and one TAG (Nts: 308-310) codon were located. The estimated molecular mass of the deduced protein was 34.65 kDa and the mature protein without signal peptide was 32.69 kDa. The estimated isoelectric point (pI) was 7.5. Chiayi-iAg was predicted to contain two transmembrane segments which were located in aa 255~277 and aa 306~328. The C-terminal portion of Chiayi-iAg was predicted to possess a potential omega (ω) site for propeptide cleavage and GPI anchor, which was localized on Ser 302 (FIG. 1).

iAg Transcripts in Transfected GF-1 Cells and iAg DNA Injected Fish Muscle

Figure 2:
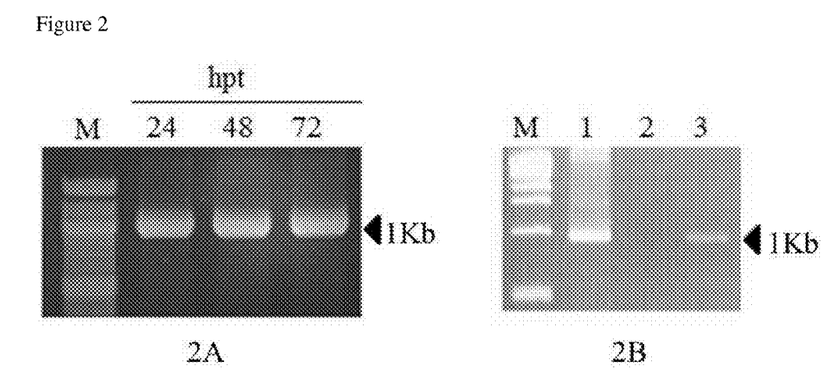
FIG. 2. iAg transcript detected by RT-PCR. A, The transcript detected from transfected GF-1 cells at each time point post transfection. Lane 1: DNA marker; Lanes 2-4: 24, 48 and 72 h post transfection (hpt), respectively. B, The transcript detected from the muscle of immunized fish at 24 hpt. M: DNA marker; Lane 1: plasmid template; Lane 2: mock plasmid injected; Lane 3: iAg plasmid injected.

RT-PCR results of GF-1 cells transfected with pcDNA3.1-optiAg showed successful identification of iAg transcript at 24 h, 48 h and 72 h post transfection (hpt) respectively (FIG. 2A). The cells transfected with same dose of mock pcDNA3.1 as negative control showed no bands. No transcripts were detectable in the non-transfected cells. Transcript of iAg was detectable in iAg immunized fish muscle sampled at 24 hpt. No transcription was observed in the mock control, pcDNA3.1 injected fish (FIG. 2B).

*E. coli* Expressed Recombinant iAg Protein

Figure 3:
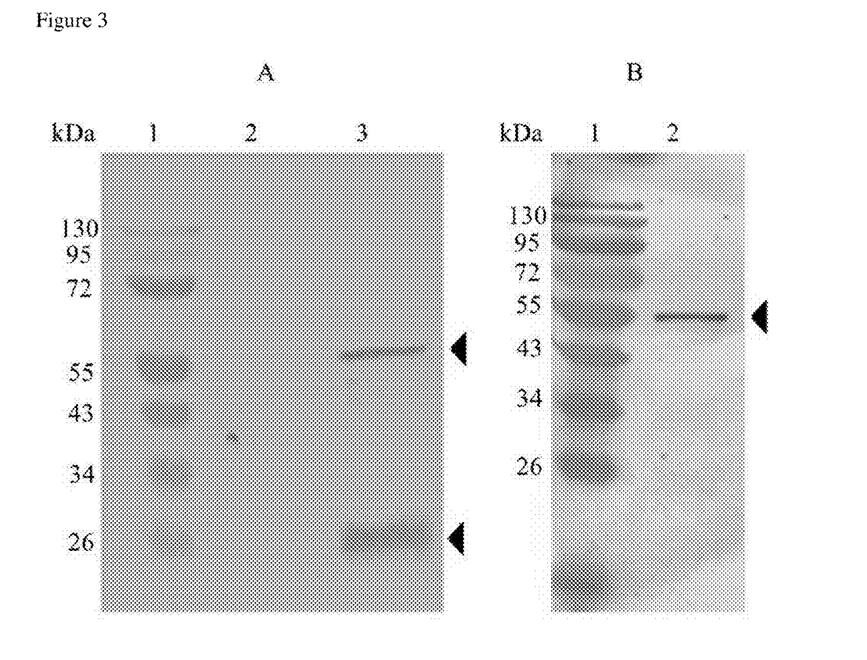
FIG. 3. Western blots showing the *E. coli* expression of recombinant iAg protein. A, Lane 1: Molecular weight standards; Lane 2: *E. coli* without IPTG induction; Lane 3: Arrowheads show 55 kDa GST-fused iAg protein and 25 kDa GST protein, respectively, in IPTG induced *E. coli* extract recognized by mouse anti-GST antibody. B, Lane 1: Molecular weight standards; Lane 2: arrow head indicates GST-fused iAg protein recognized by rabbit Ig against *C. irritans* theronts.

Western blot result demonstrated that the expression of GST-iAg fusion protein can be induced after addition of IPTG (FIG. 3A, lane 3). The fusion protein was purified by glutathione sepharose resin (BIOMAN, Taiwan). The mouse anti-GST antibody recognized the intact fusion protein which is around 55 kDa and the 25 kDa GST protein (FIG. 3A). Also, rabbit Ig against theront recognized the presence of the GST-fused iAg protein (FIG. 3B). When the rabbit pre-immune sera were used, no bands were observed. The molecular weight of the recombinant iAg was calculated by linear regression analysis of plots of the log molecular weight against electrophoretic mobility ($R^2$=0.9668). The calculated molecular weight of recombinant iAg was 32.067, closer to the estimated molecular weight of 32.69 kDa.

Expression Analysis of iAg Protein in GF-1 Cells

Figure 4:
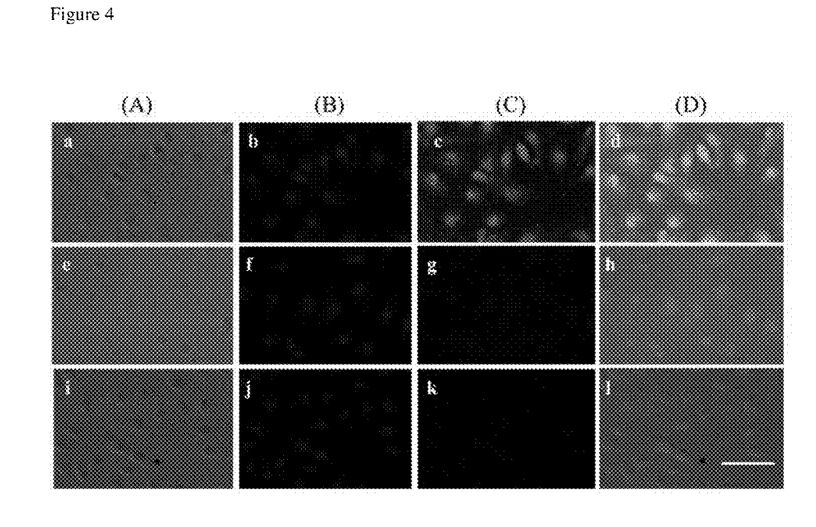
Figure 5:
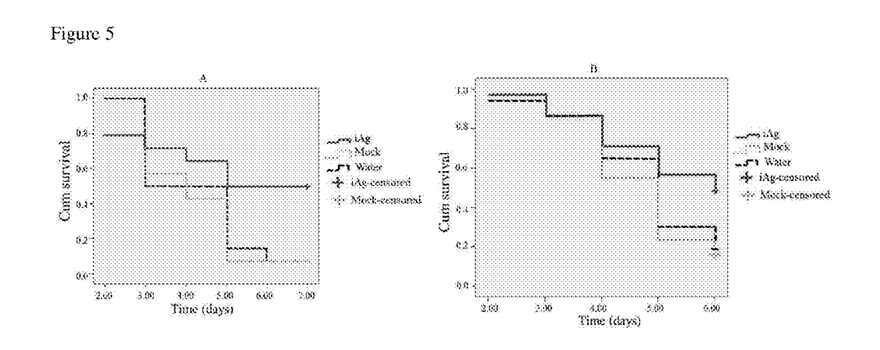

The ability of the constructed iAg plasmid to express iAg protein in GF-1 cells transfected with pcDNA3.1-optiAg was analyzed by ICC. After 48 h of transfection, only the pcDNA3.1-optiAg transfected cells expressed iAg protein, which was detected by confocal laser scanning microscope (FIG. 4c). On the other hand, the mock control transfected and non-transfected cells showed no florescence (FIGS. 4g and 4k). ICC of the pcDNA3.1-optiAg transfected cells using rabbit pre-immune Ig as the first antibody showed no florescence.

Effect of iAg Plasmid Immunization in Grouper Against *C. irritans* Challenge

As shown in Table 2, the cumulative mortalities of specific death (CMSD) of fish immunized with pcDNA3.1-optiAg was 50%, which is statistically significantly lower ($p<0.01$) compared to the control groups injected with water (93% CMSD) and pcDNA3.1 alone (93% CMSD). The highest RPS was obtained in trial I (46% RPS) in which, iAg plasmid was given at a total dose of 2 µg/g fish in twice with two days interval. Control fish that survived the parasite challenge revealed signs of *C. irritans* infection such as tiny white spots on the fish surface.

Effect of Boost with Recombinant Protein

As shown in Table 3, the RPS of iAg plasmid-immunized fingerlings boosted with recombinant iAg protein was 40%. The CMSD was significantly lower (50%) in this group ($p<0.05$) after *C. irritans* challenge. This is significantly low in comparison with those in both controls (84% CMSD).

Nano-Encapsulation

For immunization purpose, in one of the embodiment, the iAg plasmid construct was encapsulated in chitosan nanoparticles. Preparation of chitosan nanoparticles and chitosan/DNA complex is based on the following reference.

Refer to the US patent publication No. 2010086613 "chitosan vehicle and method for making same", the chitosan nanoparticles were prepared by ionic gelation. In brief, the chitosan solution (20 ml, 1% chitosan dissolved in an acetic acid solution) is gently added in to an 8 ml of tripolyphosphate (TPP) solution (0.84 mg/ml). This solution is immediately subjected to ultrasonication (29W, 4 min) at room temperature, and followed by centrifugation at 12,000 g for 45 min to remove pelleted particles. The clear supernatant contained chitosan nanoparticles. The chitosan/DNA complexes were obtained by adding a 10 ml of plasmid DNA solution (1 mg/ml) into varying amounts of the prepared chitosan solution. These mixtures were vortexed at maximum speed 20 s at room temperature. The diameters of the prepared chitosan/DNA complex fall within the range of 130~160 nm.

The immobilization antigen (iAg) used for DNA immunization in the present invention was cloned from the Chiayi isolate of *Cryptocaryon irritans* (GenBank: FJ167511). The sequence analysis of full length iAg revealed eight codons that function as termination codons in prokaryotic or in other eukaryotic organisms (seven TAA codons and one TAG codon). Hence, the codons cannot be used directly to express recombinant protein in bacteria or other eukaryotes. Among the eight termination codons, one is located in the signal peptide region. The remaining seven termination codons in the original *C. irritans* iAg gene were replaced with universal glutamine codons CAG and CAA. However, the universal glutamine codons failed to express in bacteria. Codon optimization could be performed as a way to increase protein expression in a particular cell line or organism by changing specific codons to those preferred by that species. In this way, the amino acid sequence of the vaccine protein remains the same, while the triplet of base pairs (codon) will be altered to match the codon preferences in the vaccinated organism. Accordingly, the seven termination codons in the iAg (excluding the signal peptide region) were replaced with suitable amino acids such as glycine, alanine and arginine, considering the structural and charge concerns. Also, the amino acids alanine and glycine can enhance the GC content, since they are encoded by GC-rich codons. The iAg sequence was further modified to enhance the average GC content from 36% to 47%. This codon changed iAg gene was successfully expressed in grouper fin cells and also as a GST fusion protein in bacteria.

DNA vaccine is particularly attractive to aquaculture industry for its economic, environmental and safety advantages. There are several reports indicating the effectiveness of DNA vaccines used against fish pathogens. In the present invention, the codon-changed iAg construct pcDNA3.1-optiAg was transfected in GF-1 cells and the expression of the iAg protein was confirmed by confocal laser scanning microscopy. The pcDNA3.1-optiAg was expressed in the muscle of the injected grouper confirmed by RT-PCR after immunization and the specific band corresponded well to the molecular weight of iAg. Further, the iAg protein expression in *E. coli* by plasmid pGex2T-iAg was confirmed by Western blotting. These results suggest that the recombinant iAg can be expressed correctly in vitro and in vivo, which is a prerequisite for DNA vaccination to successfully elicit immune responses.

The embodiment from the immunization and challenge tests demonstrated that iAg can provide moderate protection (46% RPS) against experimental challenge with *C. irritans*. In trial I (table 2), fish were immunized twice with 1 µg plasmid/g fish, i.e. first immunization, followed by a second immunization with the same dose 2 days later. Hence, 2 µg plasmid/g fish in total was used in trial I and the RPS was 46%. However in trial II (table 3), fish were immunized only once with 1 µg plasmid/g fish and a second dose of rec. iAg protein booster (1 µg/g fish). This time the RPS was 40% which shown no increment from the first trial. Better protection might have been attained if higher doses of iAg plasmid and recombinant iAg protein have been tried. The possible enhancing factors which could be considered are the dose of DNA vaccine, nano-encapsulation, addition of signal peptide, selecting suitable serotype and appropriate delivery method. Besides, in the other embodiments of the present invention that apart from the iAg used in this embodiment, there may be other antigen candidates in *C. irritans* which would produce better protection in infected fish.

TABLE 1

| Primers and cDNA | Sequence | Remark |
|---|---|---|
| Primer 1 | 5'-GTTCCCCTTGAACGAGGA ATTC-3' | For 18S and ITS-1 region of the rDNA of *C. irritans* |
| Primer 2 | 5'-CGCATTTCGCTGCGTTCT TC-3' | |
| Primer 3 | 5'-GATTTCATCTTTAGCTGTA ATGACATCAGC-3' | To amplify the partial nucleotide sequence of iAg |
| Primer 4 | 5'-ATCAAAATATGATCTTAAT TAGC-3' | |
| Primer 5 | 5'-TGGTCACACTTGCAGGAA CT-3' | For iAg 3'RACE |
| Primer 6 | 5'-GGATTAACATAGCACTGA ATCCTG-3' | For iAg 5'RACE |
| Primer 7 | 5'-CTTAATCGGCAGCAGCTT TT-3' | Nested reverse primer for iAg 5'RACE |
| Primer 8 | 5'-GGATCCATGGCATTTGTT AAAAAAACCGCA-3' | Codon changed iAg cloned into pcDNA3.1-optiAg and |
| Primer 9 | 5'-GAATTCTTATTT AAACAGCAGTGCAAA-3' | pGex-2t-iAg (BamHI & EcoRI site are underlined) |
| optimized immobilization antigen cDNA of *Cryptocaryon irritans* | ATGGCATTTGTTAAAAAAAC CGCAGCAGCAGATTGGAAA GGCACCTTTGTTGTTACCAA AAGCAGCTGTCTGGCAACC TGTGGTTGGAAACTGGGTA GCACCGTTGTTATTGCAGAT AAAACCGGTGTGAATACCA AAGTTACCTGGGTTGGCACC ACCCATACCACCGATACCAC CAATGTTGATGTTGCAGCAG GTAGCTGCAAATATATTAGC GCAGTTACCACCGCAGGCG GTGCAGGTACACCGGCTGA AGTTGCAAATAATAATGATG AATGCGAATTTGCAAGCGG CACCTGTACCGTTATGGGTC GTAAAGGCACCACACCGGG TACAGTTGTTTTTAATCGTG ATATGGATCTGGATACCAAA CCGCTGCAGATTCTGTATAA ACGCTTTGAAATGATTGCCA AAAGCAGCACCAGCGTTAA AGCAGCAGCCGATGCCGGT GCAGATTGTGATACCGGTGC AAGCCTGGTTGATATTACCA CCGATGCAAAACCGATTGTT GGCACCCTGAAACTGAGCA AAGCAACCTGTGATAAATGC AGCTGGGATATTACCAAAGA TCTGAAAATTACCGCAGATG CCACCAATAAATATATGGTTA CCCTGGCAGGCACCATTAAA GAAACCGCAACCGGTGATT GCAAAAATAAACTGACCGC AAGCGAAACCTGCTATGTG ACCAAAAAAGATGATAAAA CCTTTATTCTGGTGAGCTGT ACCACCCTGGATACCACAG GTAGCGGTATTCCGATTGTTA TTAGCACCGTTAATAGCAAA ACCACCCTGACCCTGACCT GGAAAGATGCAACCGCAGC CGCATGTAATGTTGTTGGTG AAGTTAGCAGCACCAGTGG TGCAAATAGCCTGAAACTGT TTACCGGTCTGAGCGTTATG CTGATTCTGACCTTTGCACT GCTGTTTAAATAA | |

TABLE 2

| Group | Immunization with | Fish BW (g) | Specific death/ total test fish | CMSD (%) | Mean CMSD (%) ± SD | RPS (%) |
|---|---|---|---|---|---|---|
| I | Water | 13~23 | 6/7 | 86 | 93 ± 9.9$^a$ | — |
|  |  | 31~44 | 7/7 | 100 |  |  |
| II | Mock plasmid | 19~27 | 7/7 | 100 | 93 ± 9.9$^a$ | 0 |
|  |  | 30~36 | 6/7 | 86 |  |  |
| III | iAg plasmid twice 2 days apart | 19~28 | 4/7 | 57 | 50 ± 9.9$^b$ | 46 |
|  |  | 33~45 | 3/7 | 43 |  |  |

Cumulative mortalities of specific death (CMSD) in the iAg plasmid-immunized (group III) and control (groups I & II) groupers after challenge were shown. Means with different superscript letters were significantly different (ANOVA and Duncan's multiple range test, p<0.01).

TABLE 3

| Group | Immunization with | Specific death/ total test fish | CMSD (%) | Mean CMSD ± SD (%) | RPS (%) |
|---|---|---|---|---|---|
| I | Water | 10/13 | 77 | 84 ± 7.54$^a$ | — |
|  |  | 10/12 | 83 |  |  |
|  |  | 11/12 | 92 |  |  |
| II | Mock plasmid | 10/12 | 83 | 84 ± 7.54$^a$ | 0 |
|  |  | 10/13 | 77 |  |  |
|  |  | 12/13 | 92 |  |  |
| III | iAg plasmid and recombinant protein 10 days apart | 6/13 | 46 | 50 ± 6.08$^c$ | 40 |
|  |  | 7/15 | 47 |  |  |
|  |  | 8/14 | 57 |  |  |

Cumulative mortalities of specific death (CMSD) in the iAg-immunized (group III) and control (groups I & II) fingerling groupers after challenge were shown. Means with different superscript letters were significantly different (ANOVA and Duncan's multiple range test, p<0.05).

DNA encapsulation in nano or microparticles was a way to enhance the uptake and to avoid degradation of DNA administered Immunization by nano-encapsulated vaccine could be practicable either via oral application or by injection. Nanoparticles were thought to be superior to microparticles because of the consistency of their size compared to microparticles. Often the compounds used to form these particles were biodegradable, which makes them attractive for immunization. A vaccine against betanodavirus in grouper was nano-encapsulated by Alarvita Biolife Company (Taipei, Taiwan) using patented substances and method. The average diameter of the nano-encapsulated particle was about 80 nm, which was much smaller compared to the 19 nm water-oil-water triple layer emulsions used in the embodiment.

In one of the embodiment, the inventors of the present invention have used Aus C isolate for water-borne challenge and the iAg DNA vaccine construct was from Chiayi isolate. The pairwise comparison of nucleotide differences in the ITS-1 region of Chiayi and Aus C showed 3.55% variation and the sequences of iAg from these two isolates share about 84% identity. But, no serum antibody response was observed for these two isolates. Hence, as far as the effect on protection efficiency was concerned, more experiment need to be done to conclude whether i-antigens could favor widely the cross-serotype protection.

DNA vaccines could widely provide both humoral and cell-mediated immune responses. In the case of intramuscularly injected DNA vaccines, myocytes appeared to be the predominant cell type transfected, and yet this method of immunization yielded potent cell-mediated protective immunity. The production of antigen by muscle cells alone was sufficient to induce CTL responses. The structures of DNA vaccine-encoded antigens capable of inducing a CTL response include whole protein, truncated protein, fusion with another protein, a string of several CTL peptides, a CTL peptide embedded in a heterologous protein, and a minimal CTL peptide. There were 9 MHC ligands/CTL epitopes identified from the iAg sequence cloned into the pcDNA3.1-optiAg, using NetCTL predictions. Various prior arts of antibody responses induced by DNA vaccines in animal models were disclosed. Certain prior arts postulated that DNA vaccines without a leading signal sequence are less immunogenic than their full-length counterparts. Conversely, prior arts confirmed that antibodies could be induced even though the protein product lacked secretion signal sequences. The ability of a DNA vaccine to produce antibody responses might depend more on its ability to produce mature protein in an appropriate conformation than on whether the protein is membrane-anchored or soluble, and whether it is targeted for secretion by conventional mechanisms. In one of the embodiment of the present invention, the iAg DNA vaccine exhibited immunogenicity although the iAg plasmid did not carry a signal sequence to express the antigen as extracellular protein. Even though this vaccine construct was sufficient to induce the immune system, but if appropriate signal sequence is incorporated in other embodiments, considerable humoral response would be expected against the target parasite, which would further enhance the effect.

In case of C. irritans vaccine in the present invention, cross-protection among different isolates was vital because the fish species encounter challenges from heterologous strains. Prior arts revealed that two different immobilization serotypes of C. irritans were immobilized by antiserum produced from the heterologous strains. Based on the immobilization titer and trophont count, it was reported that these two serotypes elicited cross-protection.

Plasmid delivery was also an essential step in promoting DNA vaccine-mediated immune response. Many different strategies have been in focus for improved in vivo DNA delivery. These include formulations such as salts, local anesthetics, lipids and sugars, and devices such as gene gun and Biojet. Delivery of antigen by incorporating in fish feeds offers the advantages of being stress free, easy to administer to large number of fish at one time, and inexpensive for the fish farmers. Unlike injection however, it was difficult to determine through oral administration exactly how much vaccine dose each fish consumed and received.

In conclusion, the present invention showed that codon change leads to the expression of parasitic iAg protein in both prokaryotic and eukaryotic cell systems. It also proved that iAg is immunogenic due to the protection albeit moderate it conferred to the immunized fish. Hence, iAg was a potent DNA vaccine in fish against infection by ciliated protozoan, C. irritans. The finding that marine fish respond to pcDNA3.1-optiAg i.m. injection indicated that iAg could be a promising candidate for DNA vaccine treatment in the disease control caused by C. irritans. The present invention was successful to provide a DNA vaccine that offers promise to develop a highly effective and protective vaccine against C. irritans.

What is claimed is:

1. An isolated and optimized immobilization antigen cDNA of *Cryptocaryon irritans* comprising the nucleotide sequence of SEQ ID NO: 10.

2. A vector comprising the isolated and optimized immobilization antigen cDNA of *Cryptocaryon irritans* of claim 1.

3. The vector of claim 2, which is pGex2T-iAg.

4. The vector of claim 2, which is pcDNA3.1-iAg.

5. A nucleic acid-based vaccine comprising the isolated and optimized immobilization antigen cDNA of *Cryptocaryon irritans* of claim 1 and a pharmaceutically acceptable adjuvant.

6. The nucleic acid-based vaccine of claim 5, which is encapsulated by water/oil/water triple layer emulsions.

7. The nucleic acid-based vaccine of claim 5, which is encapsulated by chitosan nanoparticles.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Primer 1
<220> FEATURE:
<221> NAME/KEY: misc_feature
<222> LOCATION: (1)..(22)

<400> SEQUENCE: 1
gttccccttg aacgaggaat tc                                          22

<210> SEQ ID NO 2
<211> LENGTH: 20
<212> TYPE: DNA
<213> ORGANISM: Artificial Sequence
<220> FEATURE:
<223> OTHER INFORMATION: Primer 2
<220> FEATURE:
<221> NAME/KEY: misc_feature
<222> LOCATION: (1)..(20)

<400> SEQUENCE: 2
cgcatttcgc tgcgttcttc                                             20

<210> SEQ ID NO 3
<211> LENGTH: 30
<212> TYPE: DNA
<213> ORGANISM: Artificial Sequence
<220> FEATURE:
<223> OTHER INFORMATION: Primer 3
<220> FEATURE:
<221> NAME/KEY: misc_feature
<222> LOCATION: (1)..(30)

<400> SEQUENCE: 3
gatttcatct ttagctgtaa tgacatcagc                                  30

<210> SEQ ID NO 4
<211> LENGTH: 23
<212> TYPE: DNA
<213> ORGANISM: Artificial Sequence
<220> FEATURE:
<223> OTHER INFORMATION: Primer 4
<220> FEATURE:
<221> NAME/KEY: misc_feature
<222> LOCATION: (1)..(23)

<400> SEQUENCE: 4
atcaaaatat gatcttaatt agc                                         23

<210> SEQ ID NO 5
<211> LENGTH: 20
<212> TYPE: DNA
<213> ORGANISM: Artificial Sequence
<220> FEATURE:
<223> OTHER INFORMATION: Primer 5
<220> FEATURE:
<221> NAME/KEY: misc_feature
<222> LOCATION: (1)..(20)

<400> SEQUENCE: 5
tggtcacact tgcaggaact                                             20

```
<210> SEQ ID NO 6
<211> LENGTH: 24
<212> TYPE: DNA
<213> ORGANISM: Artificial Sequence
<220> FEATURE:
<223> OTHER INFORMATION: Primer 6
<220> FEATURE:
<221> NAME/KEY: misc_feature
<222> LOCATION: (1)..(24)

<400> SEQUENCE: 6
ggattaacat agcactgaat cctg                                          24

<210> SEQ ID NO 7
<211> LENGTH: 20
<212> TYPE: DNA
<213> ORGANISM: Artificial Sequence
<220> FEATURE:
<223> OTHER INFORMATION: Primer 7
<220> FEATURE:
<221> NAME/KEY: misc_feature
<222> LOCATION: (1)..(20)

<400> SEQUENCE: 7
cttaatcggc agcagctttt                                               20

<210> SEQ ID NO 8
<211> LENGTH: 30
<212> TYPE: DNA
<213> ORGANISM: Artificial Sequence
<220> FEATURE:
<223> OTHER INFORMATION: Primer 8
<220> FEATURE:
<221> NAME/KEY: misc_feature
<222> LOCATION: (1)..(30)

<400> SEQUENCE: 8
ggatccatgg catttgttaa aaaaaccgca                                    30

<210> SEQ ID NO 9
<211> LENGTH: 27
<212> TYPE: DNA
<213> ORGANISM: Artificial Sequence
<220> FEATURE:
<223> OTHER INFORMATION: Primer 9
<220> FEATURE:
<221> NAME/KEY: misc_feature
<222> LOCATION: (1)..(27)

<400> SEQUENCE: 9
gaattcttat ttaaacagca gtgcaaa                                       27

<210> SEQ ID NO 10
<211> LENGTH: 936
<212> TYPE: DNA
<213> ORGANISM: Artificial Sequence
<220> FEATURE:
<223> OTHER INFORMATION: artificial cDNA
<220> FEATURE:
<221> NAME/KEY: misc_feature
<222> LOCATION: (1)..(936)

<400> SEQUENCE: 10
atggcatttg ttaaaaaaac cgcagcagca gattggaaag gcacctttgt tgttaccaaa    60
agcagctgtc tggcaacctg tggttggaaa ctgggtagca ccgttgttat tgcagataaa   120
accggtgtga ataccaaagt tacctgggtt ggcaccaccc ataccaccga taccaccaat   180
gttgatgttg cagcaggtag ctgcaaatat attagcgcag ttaccaccgc aggcggtgca   240
```

-continued

| | | | | | |
|---|---|---|---|---|---|
| ggtacaccgg | ctgaagttgc | aaataataat | gatgaatgcg | aatttgcaag | cggcacctgt | 300 |
| accgttatgg | gtcgtaaagg | caccacaccg | ggtacagttg | tttttaatcg | tgatatggat | 360 |
| ctggatacca | aaccgctgca | gattctgtat | aaacgctttg | aaatgattgc | caaaagcagc | 420 |
| accagcgtta | aagcagcagc | cgatgccggt | gcagattgtg | ataccggtgc | aagcctggtt | 480 |
| gatattacca | ccgatgcaaa | accgattgtt | ggcaccctga | aactgagcaa | agcaacctgt | 540 |
| gataaatgca | gctgggatat | taccaaagat | ctgaaaatta | ccgcagatgc | caccaataaa | 600 |
| tatatggtta | ccctggcagg | caccattaaa | gaaaccgcaa | ccggtgattg | caaaaataaa | 660 |
| ctgaccgcaa | gcgaaacctg | ctatgtgacc | aaaaaagatg | ataaaaccttt | tattctggtg | 720 |
| agctgtacca | ccctggatac | cacaggtagc | ggtattccga | ttgttattag | caccgttaat | 780 |
| agcaaaacca | ccctgacccct | gacctggaaa | gatgcaaccg | cagccgcatg | taatgttgtt | 840 |
| ggtgaagtta | gcagcaccag | tggtgcaaat | agcctgaaac | tgtttaccgg | tctgagcgtt | 900 |
| atgctgattc | tgacctttgc | actgctgttt | aaataa | | | 936 |